(12) United States Patent
Stewart (10) Patent No.: US 6,945,958 B2
(45) Date of Patent: Sep. 20, 2005

(54) SAFETY NEEDLE APPARATUS

(75) Inventor: Bradley M. Stewart, Westfield, MA (US)

(73) Assignee: Sherwood Services AG, Schauffhausen (CH)

( * ) Notice: Subject to any disclaimer, the term of this patent is extended or adjusted under 35 U.S.C. 154(b) by 200 days.

(21) Appl. No.: 10/344,059

(22) PCT Filed: Oct. 18, 2002

(86) PCT No.: PCT/US02/33409

§ 371 (c)(1),
(2), (4) Date: Feb. 6, 2003

(87) PCT Pub. No.: WO03/041766

PCT Pub. Date: May 22, 2003

(65) Prior Publication Data

US 2004/0015136 A1 Jan. 22, 2004

Related U.S. Application Data (60) Provisional application No. 60/332,171, filed on Nov. 14, 2001.

(51) Int. Cl.$^7$ ................................................ A61M 5/00
(52) U.S. Cl. ...................... 604/110; 604/198; 604/263; 604/232; 222/325
(58) Field of Search ................................ 222/325–327, 222/386; 604/110, 192, 197, 198, 263, 162, 164.08, 232, 234

(56) References Cited

U.S. PATENT DOCUMENTS

| | | | |
|---|---|---|---|
| 4,801,295 A | * | 1/1989 | Spencer ...................... 604/198 |
| 4,998,924 A | | 3/1991 | Ranford ...................... 604/798 |
| 5,024,660 A | | 6/1991 | McNaughton ............... 604/110 |

FOREIGN PATENT DOCUMENTS

| | | | |
|---|---|---|---|
| EP | 0 369 619 | 5/1990 | ............ A61M/5/32 |
| EP | 0 350 186 | 10/1990 | ............ A61M/5/32 |
| WO | WO 92/18183 | 10/1992 | ............ A61M/5/32 |

* cited by examiner

*Primary Examiner*—Nicholas D. Lucchesi
*Assistant Examiner*—Cris L. Rodriguez
(74) *Attorney, Agent, or Firm*—Mark S. Leonardo; Peter B. Sorell; Brown Rudnick Berlack Israels LLP (57) ABSTRACT

A safety needle apparatus having a needle is provided that includes a first cylinder extending from a proximal end to a distal end thereof and defining a longitudinal axis. The first cylinder further defines at least one longitudinal keyway in a side wall thereof and at least one keyslot disposed adjacent the distal end of the first cylinder. The keyslot is rotationally spaced apart from the at least one keyway relative to the longitudinal axis. The keyway includes a raised surface relative to and disposed adjacent the distal end of the first cylinder. A second cylinder is mounted for relative movement with the first cylinder and defines at least one radially projecting key adjacent a proximal end thereof. The key is configured for axial movement along the keyway such that the second cylinder is movable between an activated position, whereby the key is releasably engaged with a proximal end of the keyway to expose the needle, and a transport position, whereby the key is releasably disposed adjacent the distal end of the first cylinder via an interference engagement with the raised surface of the first cylinder to releasably enclose the needle within the second cylinder. The second cylinder is further movable from the transport position to a locked position, whereby the key is rotated relative to the first cylinder for fixed disposal within the keyslot to fixedly enclose the needle within the second cylinder.

20 Claims, 12 Drawing Sheets

SAFETY NEEDLE APPARATUS

This application is a National Stage of International Application No. PCT/US02/33409, filed Oct. 18, 2002, which claims benefit of U.S. Provisional Application No. 60/332,171, filed Nov. 14, 2001, now abandoned.

BACKGROUND

1. Technical Field

The present disclosure generally relates to the field of medical needle assemblies for the administration of fluids, and more particularly, to safety shields that prevent hazardous exposure to a needle during use and transport.

2. Description of the Related Art

Problems associated with inadvertent needle sticks are well known in the art of fluid sampling, percutaneous medication injection and other medical procedures involving the use of medical needles. Significant attention is focused on health risks associated with hazardous needle exposure due to the contemporary sensitivity of exposure to AIDS, Hepatitis and other serious blood-borne pathogen exposures. These risks are some of the most prevalent occupational health hazards among healthcare professionals. These professionals are in danger of contracting such blood-borne pathogens from infected patients by inadvertent needle sticks from a contaminated needle employed during dental, medical, laboratory, etc. procedures.

Many known needle shielding devices have been used in an attempt to overcome the health hazards associated with inadvertent or undesired needle stick from a contaminated needle. Some of these devices utilize a separate shielding cap mounted over the needle after use, while other devices employ pivoting, spring activated telescoping shields, etc. These type of structure, however, can require button or lever activation that is prone to accidental engagement resulting in hazardous needle exposure.

In an exemplary dental needle application, a syringe dispenses medication from a medical cartridge that is supported by a barrel or the like. A double-ended needle is mounted to the barrel and has a proximal end that penetrates a seal of the medical cartridge. Medication is delivered by the needle through a distal end thereof to a patient via manipulation of a plunger. Upon removal of the distal end of the needle from the patient, a shield mounted to the barrel is slid from a retracted position to an extended position to cover the needle. Some devices allow the shield to freely slide between the extended and the retracted positions. These configurations, however, may disadvantageously interfere with a procedure or expose the distal end of the needle after use resulting in hazardous exposure to the needle.

Other shield devices employ locking structure to permanently lock the shield in the extended position. See, e.g., U.S. Pat. No. 5,024,660. These type devices, however, do not allow re-exposure of the distal end of the needle for multiple injection procedures, during transport, etc. Further, these devices may disadvantageously require complex relative movements of the barrel and shield to effect locking.

The above mentioned devices may suffer from additional drawbacks such as needle bending during use and moisture buildup on the shield, which can prevent visual inspection of needle travel during a procedure.

Therefore, it would be desirable to overcome the disadvantages and drawbacks of the prior art with a safety needle apparatus that is easily employed to prevent hazardous exposure to a needle during use, transport and upon completion of a procedure to facilitate disposal thereof. It would be highly desirable if the safety needle apparatus was designed to prevent needle bending during use and moisture buildup on a shield of the safety needle apparatus. It is contemplated that the safety needle apparatus is easily and efficiently fabricated.

SUMMARY

Accordingly, a safety needle apparatus is provided that is easily employed to prevent hazardous exposure to a needle during use, transport and upon completion of a procedure to facilitate disposal thereof for overcoming the disadvantages and drawbacks of the prior art. Desirably, the safety needle apparatus is designed to prevent needle bending during use and moisture buildup on a shield of the safety needle apparatus. The safety needle apparatus is easily and efficiently fabricated. The present disclosure resolves related disadvantages and drawbacks experienced in the art.

One of the advantages of the present disclosure is the ability to manipulate the safety needle apparatus to a transport position. For example, during administration of anesthetic medication during a dental procedure, a clinician may desire to set the needle aside and subsequently use the needle to administer additional injections. The safety needle apparatus allows the clinician to slide a shield of the safety needle apparatus in the distal direction into the transport position to perform multiple injections.

The transport position is a releasably retained position and the needle is protected from inadvertent exposure. It is contemplated that an arrow will be molded into a barrel of the safety needle apparatus and universal lock or unlock symbols will be molded on the shield. In the transport position, the arrow of the barrel will be lined up with the unlocked symbol indicating that the safety needle apparatus is in the transport position and not a permanent final lock position. The shield can be moved between the transport position to an active position as deemed necessary by the clinician for additional injections.

During the administration of the medication, additional medication cartridges may be required. By placing the shield in the transport position the safety needle apparatus can be safely removed from a syringe holder and the used cartridge removed and replaced with a new cartridge. The safety needle apparatus is reattached and employed for subsequent injections.

Another advantage of the present disclosure is the ability to manipulate the safety needle apparatus to a final lock position. Upon completion of the desired injections, the shield can be manipulated to the permanent final lock position. Once in the final lock position, the shield can no longer be retracted to expose the needle and the safety needle apparatus is safe for removal and disposal. In the transport position, the clinician can place the safety needle apparatus in the final lock position by grasping the shield and rotating, for example, approximately 45° in either the clockwise or counter clockwise direction.

The clinician may receive confirmation that the safety needle apparatus is in the final lock position by tactile and visual attributes. Tactilely, the clinician will feel the snap as keys of a lock ring of the shield enter the final lock position. Visually, the arrow on the barrel will be aligned with one of the locked symbols disposed adjacent to the unlocked symbol. It is contemplated that there will also be an audible sensation as the keys snap into the final locked position.

It is contemplated that the safety needle apparatus is available in various lengths for adaptability to a standard barrel. It is further contemplated that the needle lengths may vary.

Other advantages of the present disclosure include manipulation of the safety needle apparatus to the transport and final lock positions without the use of buttons or levers. This configuration avoids associated risks that could result in hazardous exposure to the needle. The shield can be designed with a small inner diameter cylindrical surface at its distal end. Needles that are intentionally or unintentionally bent by the user during injections will be contained within this inner diameter cylindrical surface. This feature maintains the point of the needle facing forward and minimizes piercing of the side wall of the shield. This feature also allows the clinician to re-enter the active position without causing additional bending of the needle or puncturing of the shield.

A cylindrical section can be molded on the barrel near the distal end. The cylindrical section is designed to create a contact fit with the inner diameter surface of the distal end of the shield. This contact fit serves as a moisture barrier when the shield is retracted and the needle is exposed. By blocking the path of the moisture from the patient's mouth to the inside of the shield, the occurrence of shield fogging can be eliminated. Desirably, the safety needle apparatus has a narrow, low profile design allowing minimally restricted access to the patient's mouth and gum areas and allows a clear line of site for injections.

Another advantage of the safety needle apparatus of the present disclosure is avoidance of a clinician's hands being in the direct path of an exposed needle. This is particularly beneficial when the clinician attempts to remove a cap or sheath from a distal end of the safety needle apparatus. For example, the sheath may engage the shield of the safety needle apparatus in an interference fit. The clinician can manipulate the sheath in the distal direction such that the shield slides forward with the sheath and into the transport position. Once the shield is in the transport position, continued application of force on the sheath will detach the sheath from the shield and allow removal. The distal end of the needle will be surrounded by the shield to avoid accidental needlesticks. In another example, the clinician can slide the shield into the transport position by grasping the shield and sliding it in the distal direction. Once in the transport position, the sheath can be safely removed because the protective shield surrounds the needle.

In one particular embodiment, in accordance with the principles of the present disclosure, a safety needle apparatus having a needle is provided that includes a first cylinder extending from a proximal end to a distal end thereof and defining a longitudinal axis. The first cylinder further defines at least one longitudinal keyway in a side wall thereof and at least one keyslot disposed adjacent the distal end of the first cylinder. The keyslot is rotationally spaced apart from the at least one keyway relative to the longitudinal axis. The keyway includes a raised surface relative to and disposed adjacent the distal end of the first cylinder. A second cylinder is mounted for relative movement with the first cylinder and defines at least one radially projecting key adjacent a proximal end thereof. The key is configured for axial movement along the keyway such that the second cylinder is movable between an activated position, whereby the key is releasably engaged with a proximal end of the keyway to expose the needle, and a transport position, whereby the key is releasably disposed adjacent the distal end of the first cylinder via an interference engagement with the raised surface of the first cylinder to releasably enclose the needle within the second cylinder. The second cylinder is further movable from the transport position to a locked position, whereby the key is rotated relative to the first cylinder for fixed disposal within the keyslot to fixedly enclose the needle within the second cylinder.

In an alternate embodiment, the first cylinder includes a barrel and the second cylinder includes a shield mounted to an outer surface of the barrel. The second cylinder may include an elongated shield configured to enclose the needle and a locking ring mounted to a proximal end of the shield. The locking ring defines the key about an inner circumferential surface thereof. The shield may include at least one proximally extending tab that facilitates mounting of the shield within the lock ring. The shield can include a plurality of proximally extending tabs that facilitate mounting of the shield within the lock ring. The tab may be flexibly cantilevered from the shield.

The locking ring may define a plurality of keys about the inner circumferential surface thereof and the first cylinder further defines a plurality of keyslots for disposal of the keys therein. The locking ring may mount with the shield via disposal of the plurality of keys within a plurality of axial slots defined by the proximal end of the shield. The plurality of keys may be equidistantly spaced for corresponding disposal within the plurality of axial slots of the shield.

Alternately, the second cylinder is movable from the transport position to the locked position such that the plurality of keys are rotatable in a clockwise direction and a counter clockwise direction relative to the first cylinder for fixed disposal within the plurality of keyslots to fixedly enclose the needle within the second cylinder.

The proximal end of the shield can include a radial lip that engages the lock ring to facilitate retention therewith. The first cylinder may define a reduced diameter cylindrical portion extending from the distal end thereof. A distal end of the second cylinder is configured and dimensioned to receive an outer surface of the cylindrical portion of the first cylinder in a contacting engagement. The cylindrical portion of the first cylinder may have a circumferential lip that engages the distal end of the second cylinder in an interference fit configured to form a moisture barrier.

Alternately, the first cylinder and the second cylinder include visual indicia that cooperate to provide a visual indication that the second cylinder is in the locked position.

The proximal end of the first cylinder can include at least one radially projecting tab. The tab of the first cylinder is configured for receipt within a cammed slot of a syringe plunger adapter for mounting therewith.

In another alternate embodiment, a dental safety needle apparatus having a double-ended needle cannula includes a barrel extending from a proximal end to a distal end thereof and defining a longitudinal axis. The barrel further defines a pair of diametrically disposed longitudinal keyways in a sidewall thereof and a plurality of keyslots disposed adjacent the distal end of the barrel. The keyslots are rotationally spaced apart from the keyways relative to longitudinal axis. The keyways include a raised surface relative to and disposed adjacent to the distal end of the barrel. The barrel have a reduced diameter barrel tip extending from the distal end thereof.

A shield is mounted for relative movement with the barrel and includes a lock ring mounted to a proximal end thereof. The lock ring has a pair of diametrically disposed radially projecting keys. The keys are configured for axial slidable movement along the keyways of the barrel such that the shield is movable between an activated position, whereby the keys are releasably engaged with proximal ends of the keyways to expose the double-ended needle cannula, and a transport position, whereby the keys are releasably disposed adjacent the distal end of the barrel via an interference engagement with the raised surface of the barrel to releasably enclose the double-ended needle cannula within the shield. The shield is further movable from the transport position to a locked position such that the keys are rotatable in a clockwise direction and a counter clockwise direction relative to the barrel for fixed disposal within the plurality of keyslots to fixedly enclose the double-ended needle cannula within the shield. The lock ring includes raised longitudinal ribs circumferentially disposed thereabout.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

DETAILED DESCRIPTION OF EXEMPLARY EMBODIMENTS

The exemplary embodiments of the safety needle apparatus and methods of operation disclosed are discussed in terms of medical needle assemblies for the administration of fluids, and more particularly, in terms of a dental safety needle apparatus that is easily employed to prevent hazardous exposure to a needle during use, transport and upon completion of a procedure to facilitate disposal thereof. It is contemplated that the needle may be shielded during use including storage, transport, fluid infusion and/or collection, subsequent thereto, etc. It is envisioned that the present disclosure, however, finds application to a wide variety of cannula needles and devices for the infusion of preventive medications, medicaments, therapeutics, etc. as well as injections employed during procedures relating to phlebotomy, orthopedic, digestive, intestinal, urinary, veterinary types, etc., to a subject. It is also envisioned that the present disclosure may be employed for collection of body fluids including those employed during procedures relating to phlebotomy, digestive, intestinal, urinary, veterinary, etc. It is contemplated that the safety needle apparatus may be utilized with other medical needle applications including phlebotomy devices, catheters, catheter introducers, guide wire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the safety needle apparatus. According to the present disclosure, the term "clinician" refers to an individual administering an infusion, performing fluid collection, installing or removing a safety needle apparatus and may include support personnel.

The following discussion includes a description of the safety needle apparatus, followed by a description of an exemplary method of operating the safety needle apparatus in accordance with the principles of the present disclosure. Reference will now be made in detail to the exemplary embodiments of the disclosure, which are illustrated in the accompanying figures.

The component parts of the safety needle apparatus are fabricated from materials suitable for medication injections, such as, for example, polymerics or metals, such as stainless steel, depending on the particular medical needle application and/or preference of a clinician. Semi-rigid and rigid polymerics are contemplated for fabrication, as well as resilient materials, such as molded medical grade polypropylene. One skilled in the art, however, will realize that other materials and fabrication methods suitable for assembly and manufacture, in accordance with the present disclosure, also would be appropriate.

Turning now to the figures, wherein like components are designated by like reference numerals throughout the several views. Referring initially to FIGS. 1–11, there is illustrated a dental safety needle apparatus 20 including a double-ended needle cannula 26, constructed in accordance with the principals of the present disclosure. Needle cannula 26 is suitably configured for medical, dental, laboratory, etc. applications to perform infusion, fluid collection, etc. Dental safety needle apparatus 20 is advantageously configured to prevent hazardous exposure to needle cannula 26 during use, transport and upon completion of a procedure to facilitate disposal thereof, as will be discussed below.

Dental safety needle apparatus 20 includes a first cylinder, such as, for example, barrel 22 extending from a proximal end 21 to a distal end 23 and defining a longitudinal axis x. Barrel 22 further defines keyways 32 in a side wall 25 thereof. It is contemplated that one or a plurality of keyways 32 may be employed. Keyslots 36 are disposed adjacent distal end 23 of barrel 22 and rotationally spaced apart from keyways 32 relative to longitudinal axis x. It is contemplated that one or a plurality of keyslots 36 may be employed. Keyways 32 include a raised surface, such as, for example, releasable stop 40 relative to and disposed adjacent distal end 23. It is envisioned that releasable stop 40 may be variously positioned with keyway 32.

A second cylinder, such as, for example, shield 28 is mounted to an outer surface of barrel 22 for relative movement therewith and includes a lock or locking ring 24 mounted to a proximal end 29 of shield 28. Lock ring 24 defines radially projecting keys, including long keys 46 and short keys 48. Long keys 46 are configured for axial movement along keyways 32 such that shield 28 is movable between an activated position (FIG. 17), whereby long keys 46 are releasably engaged with releasable stop 40 to expose a distal end 72 of needle 26, and a transport position (FIG. 18), whereby long keys 46 are releasably disposed adjacent distal end 23 of barrel 22 via an interference engagement with releasable stop 40 to releasably enclose distal end 72 of needle 26 within shield 28. Shield 28 is further movable from the transport position to a final locked position (FIG. 19), whereby long keys 46 are rotated relative to barrel 22 for fixed disposal within keyslots 36 to fixedly enclose distal end 72 of needle 26 within shield 28. It is envisioned that one or a plurality of keys may be employed. It is further envisioned that the first cylinder and the second cylinder may interchangeably include the barrel or the shield.

Dental safety needle apparatus 20 is advantageously configured to shield dental needles and protect clinicians, including dentists and their assistants from inadvertent needle sticks during the attachment and removal of dental safety needle apparatus 20 from a syringe adaptor during use, including multiple injections and transport, as discussed. Additionally, dental safety needle apparatus 20 includes a final lock position to ensure that needle 26 is not inadvertently exposed after use. Dental safety needle apparatus 20 device presented can be used with reusable plastic syringe adaptors.

Figure 1:
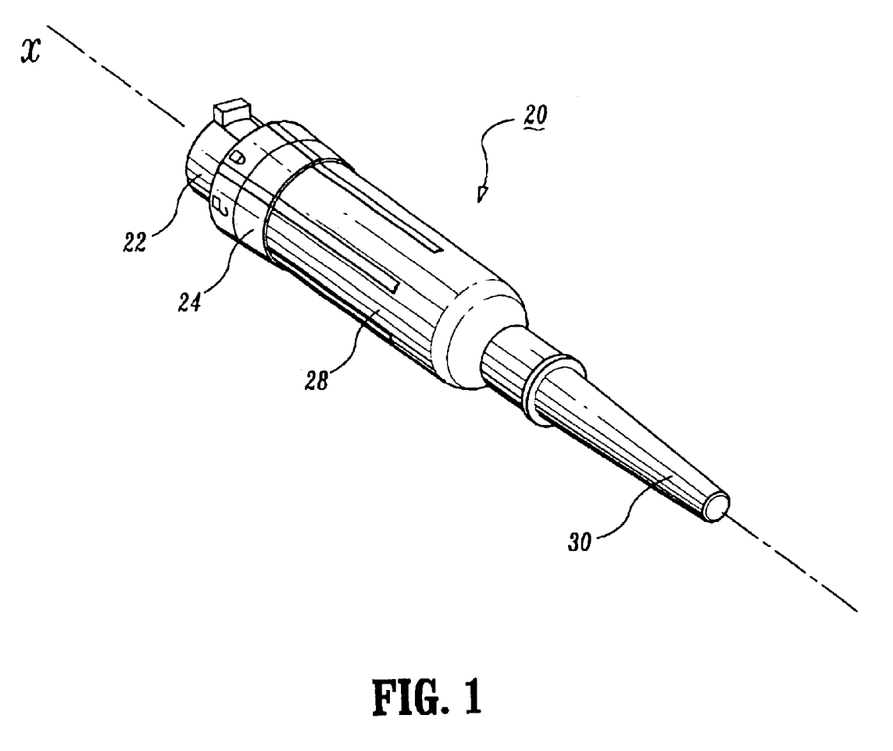
FIG. 1 is a perspective view of one embodiment of a safety needle apparatus, in accordance with the principles of the present disclosure.
Figure 2:
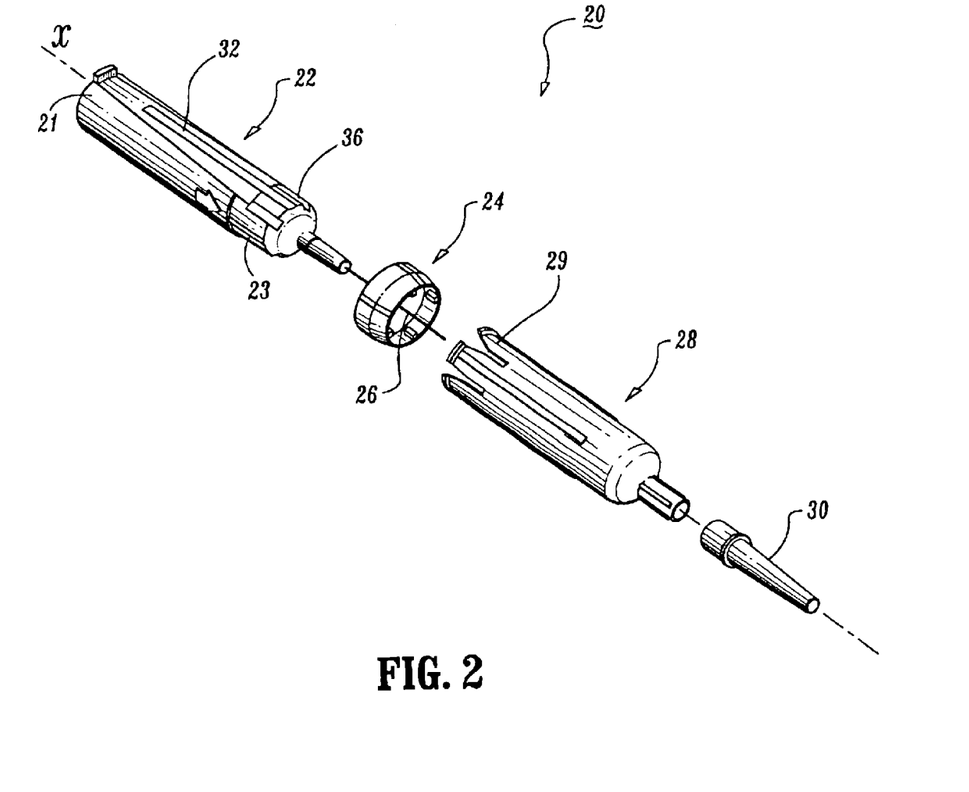
FIG. 2 is a perspective view of the safety needle apparatus shown in FIG. 1, with parts separated.
Figure 3:
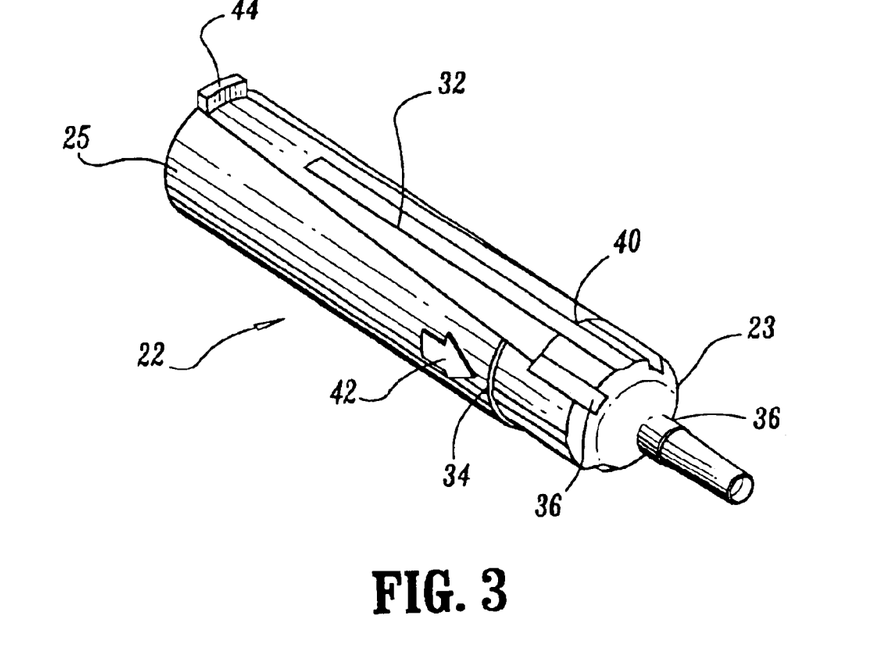
FIG. 3 is a perspective view of a barrel of the safety needle apparatus shown in FIG. 1.
Figure 4:
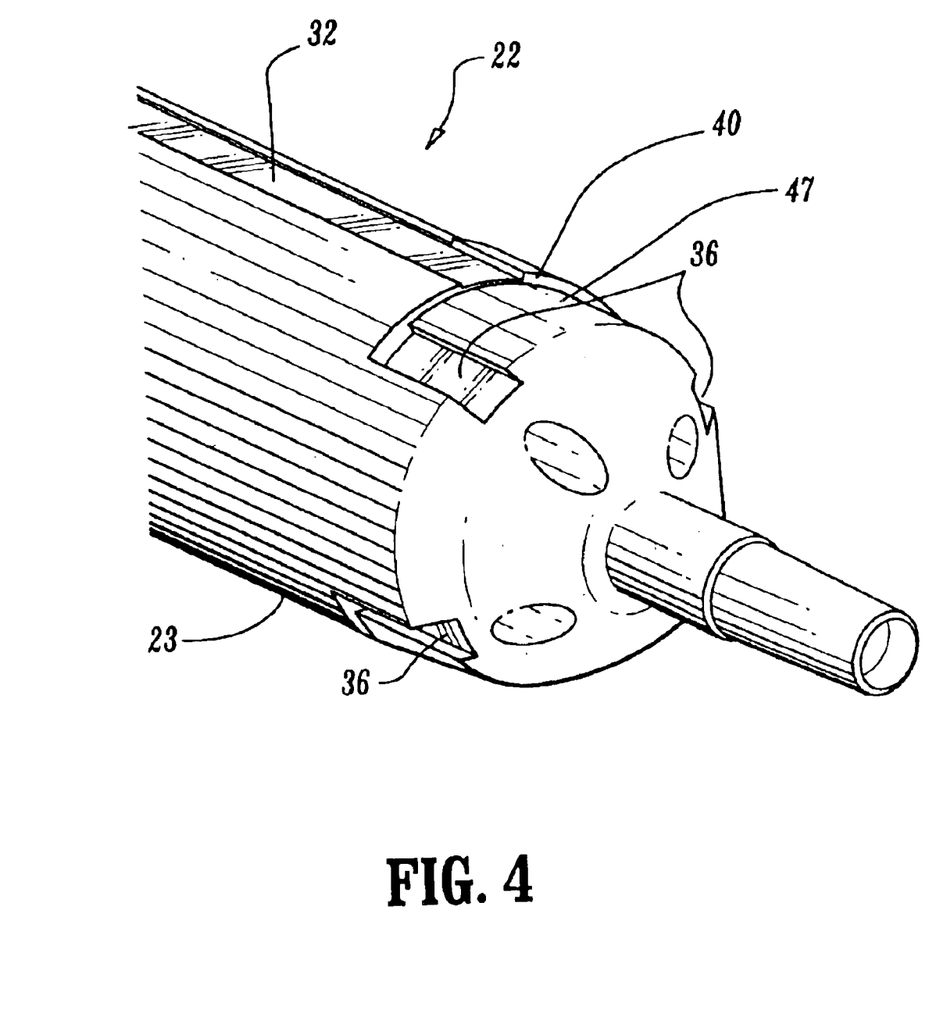
FIG. 4 is an enlarged cut-away perspective view of a distal end of the barrel shown in FIG. 1.
Figure 5:
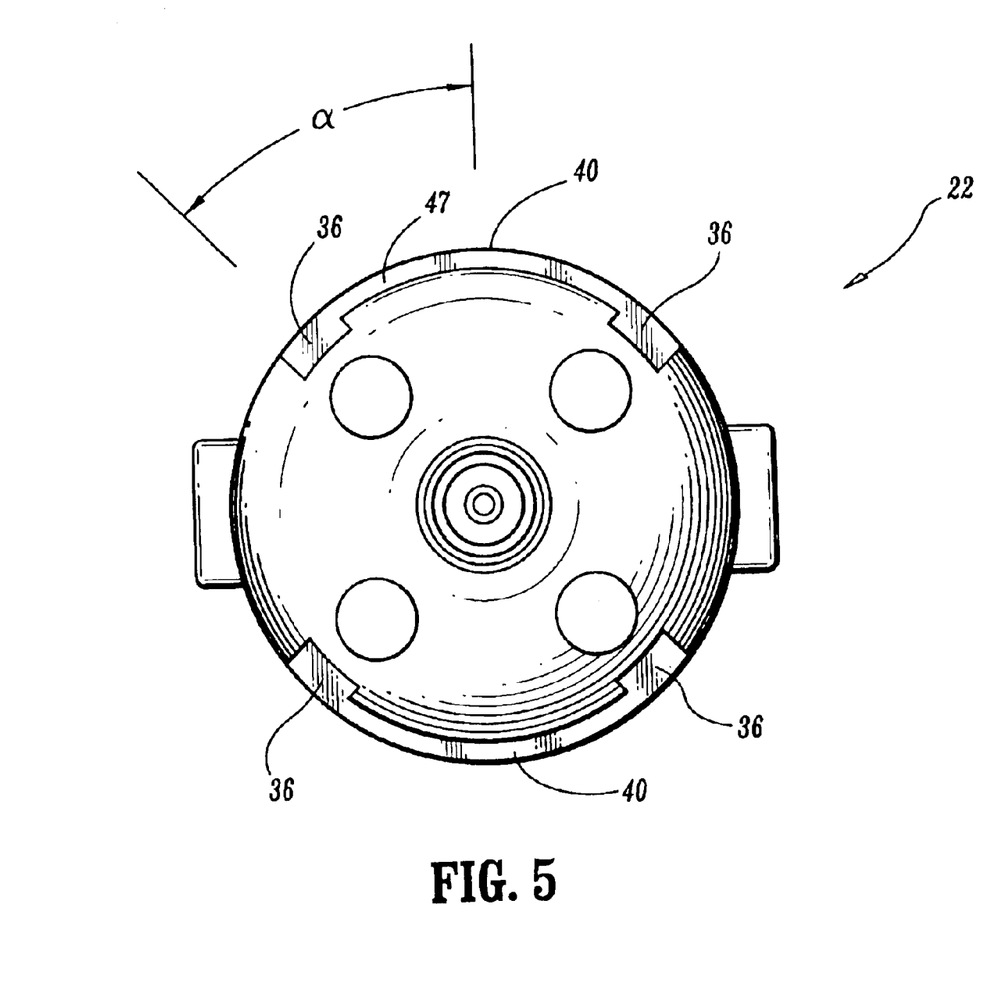
FIG. 5 is an enlarged front view of the barrel shown in FIG. 1.

Referring to FIGS. 3–5, barrel 22 includes keyways 32 diametrically disposed along a length thereof. Keyways 32 may be variously disposed about barrel 22. Keyways 32 receive long keys 46 to facilitate relative slidable movement of lock ring 24 and barrel 22. Keyways 32 provide sufficient frictional resistance to maintain long keys 46 adjacent a proximal end thereof such that shield 28 is held in the active position. It is contemplated that long keys 46 may be frictionally maintained at various positions along keyways 32 or that short keys 48 may be frictionally held therewith.

A radial stop 34 prevents shield 28 from traveling beyond a designated position so that shield 28 cannot be removed. Radial stop 34 prevents travel of shield 28 beyond stop 34 via engagement with shield 28, discussed below.

Locking slots 36 are formed in a distal end of barrel 22 and configured to receive long keys 46, which become trapped therein to lock shield 28 in the final lock position.

From the transport position, shield 28 and lock ring 24 are manipulated such that long keys 46 are rotated about barrel 22 at an angle α relative to longitudinal axis x, which spans from keyway 32 to keyslot 36. For example, shield 28 is manipulated such that keys 46 are rotated approximately 45 degrees, in the clockwise or counter-clockwise direction. After long key 46 moves distally beyond releasable stop 40, long key 46 engages a key surface 47. As shield 28 and lock ring 24 are manipulated, key 46 travels along key surface 47 and is fixedly disposed in keyslot 36 for locking shield 28 in the final locked position. Key surface 47 has a uniform arcuate surface to facilitate free sliding of long keys 46 therealong. It is contemplated that key surface 47 may provide resistance to movement of long keys 46 by, for example, friction, a raised surface, etc.

Barrel 22 includes visual indicia, such as, for example an arrow 42 that cooperates with visual indicia of shield 28 to indicate whether shield 28 is in the transport position or the final lock position, as will be discussed. Tabs 44 are diametrically disposed about proximal end 21 of barrel 22 to facilitate attachment with a syringe adaptor, as discussed below.

Figure 6:
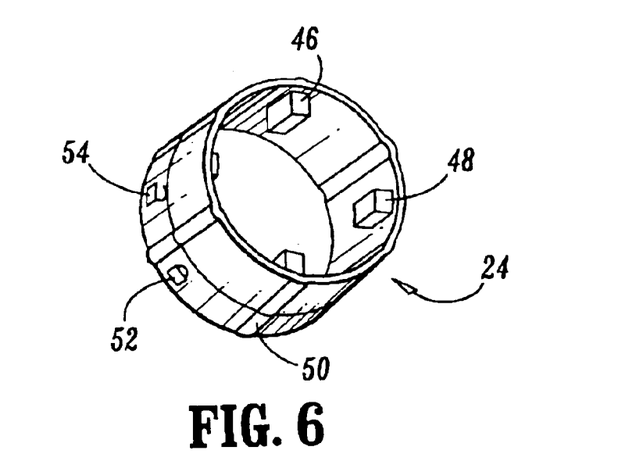
FIG. 6 is a perspective view of a lock ring of the safety needle apparatus shown in FIG. 1.
Figure 7:
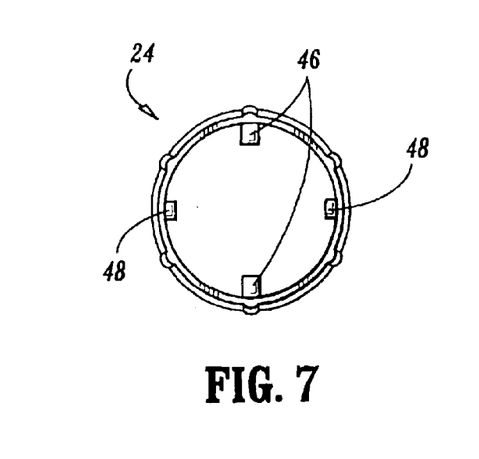
FIG. 7 is a front view of the lock ring shown in FIG. 6.
Figure 8:
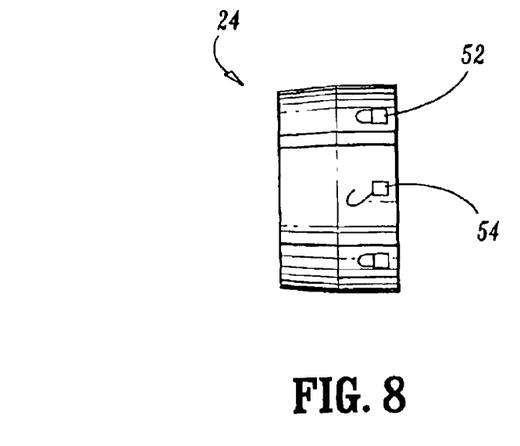
FIG. 8 is a side view of the lock ring shown in FIG. 6.

Referring to FIGS. 6–8, long keys 46 and short keys 48 of lock ring 24 are equidistantly spaced about an inner circumferential surface thereof and guided within axial slots 58 of shield 28 for attachment therewith. Shield 28 may include one or a plurality of slots 58. Raised longitudinal ribs 50 are disposed about an outer circumferential surface of lock ring 24. Ribs 50 are configured to facilitate handling and manipulation of shield 28. Universal lock symbols 52 and unlocked symbols 54 are disposed on the outer circumferential surface of lock ring 24 to provide a visual indicia to a clinician in cooperation with arrow 42, that shield 28 is in the transport position or the final lock position. It is contemplated that lock ring 24 may have other geometric configurations, such as, for example, rectangular, elliptical, etc.

Figure 9:
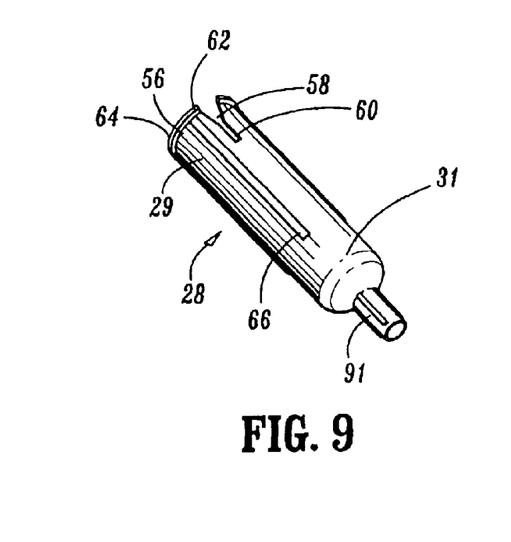
FIG. 9 is a perspective view of a shield of the safety needle apparatus shown in FIG. 1.
Figure 10:
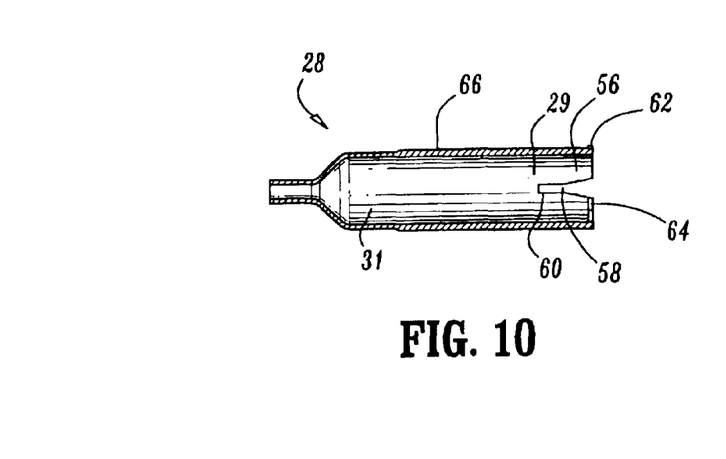
FIG. 10 is a cross-sectional side view of the shield shown in FIG. 9.

Referring to FIGS. 9 and 10, shield 28 includes tabs 56 that extend from proximal end 29 thereof to facilitate mounting with lock ring 24. Tabs 56 are flexibly cantilevered and compressible to facilitate attachment with lock ring 24. Upon compression of tabs 56, lock ring 24 slides onto shield 28. Axial slots 58 are disposed between tabs 56 and are configured to guide long keys 46 and short keys 48 of lock ring 24 during attachment. Axial slots 58 have closed distal ends 60 that interfere with long keys.46 and short keys 48 to restrict distal movement of lock ring 24 upon attachment to shield 28.

Shield 28 includes an external lip 62 configured to interfere with a proximal edge of lock ring 24 restricting proximal movement of lock ring 24 upon attachment. An internal lip 64 is configured to prevent removal of shield 28 from barrel 22 upon attachment. Raised longitudinal ribs 66 are disposed about the circumference and along the longitudinal length of shield 28 to facilitate handling and manipulation of lock ring 24 and shield 28.

Figure 20:
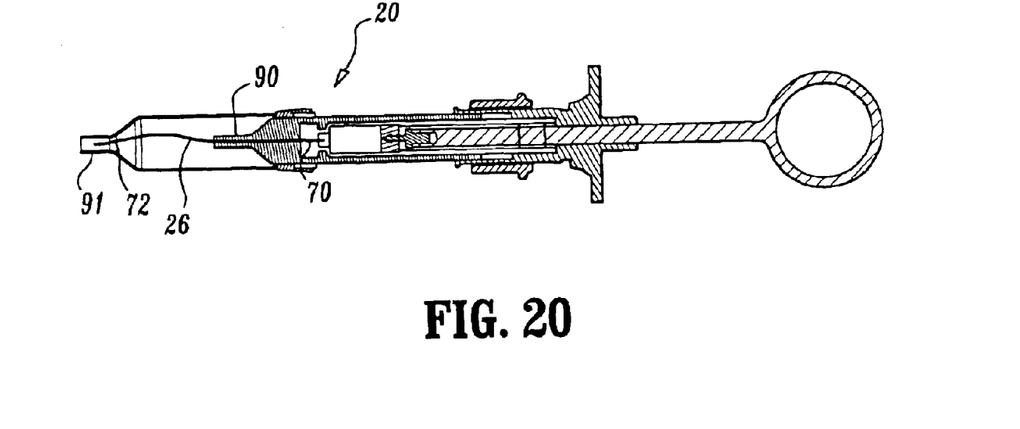
FIG. 20 is a side cross-sectional view of the safety needle apparatus shown in FIG. 1 mounted with a syringe adapter.
Figure 21:
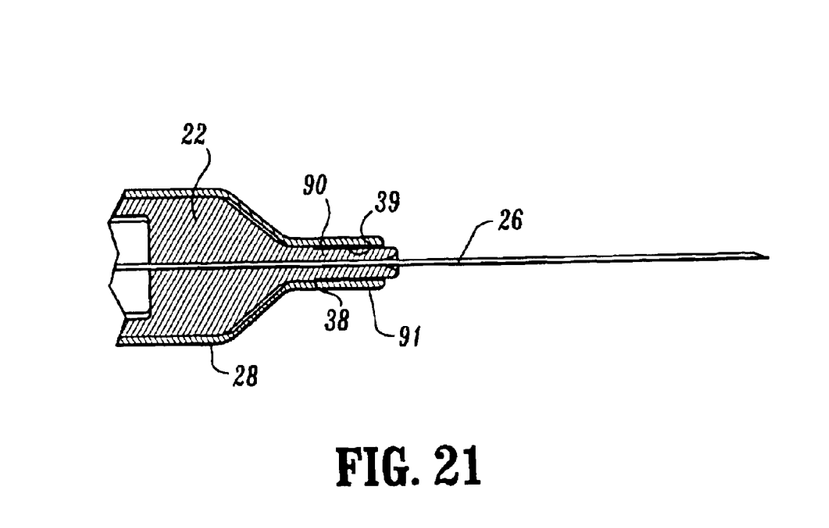
FIG. 21 is a side cutaway cross-sectional view of an alternate embodiment of a distal end of the safety needle apparatus shown in FIG. 1.

Barrel 22 defines a reduced diameter cylindrical portion 90 extending from distal end 23, as shown in FIGS. 20 and 21. A distal end 31 of shield 28, such as, for example, cylindrical portion 91 is configured and dimensioned to receive an outer surface of cylindrical portion 90 in a contacting engagement. Cylindrical portion 90 has a circumferential lip 38 that engages cylindrical portion 91 in an interference fit configured to form a moisture barrier. This configuration advantageously blocks the path of moisture from a subject's mouth to the interior of shield 28. In the event that shield 28 is fabricated from a transparent or semi-transparent material, fogging is substantially avoided or eliminated.

Dental safety needle apparatus 20 is assembled by compressing tabs 56 of shield 28 and sliding lock ring 24 thereon. Keys 46, 48 of lock ring 24 slide within slots 58 of shield 28. Lock ring 24 is disposed about shield 28 and movement of lock ring 24 is prevented in the distal direction by interference between keys 46, 48 and distal end 60 of slots 58. Lock ring 24 is prevented from proximal movement by interference with external lip 62. Shield 28 and lock ring 24 are attached to barrel 22 by guiding long keys 46 within keyways 32 of barrel 22. Internal lip 64 slides over radial stop 34 for retention of shield 28 with barrel 22. Shield 28 and lock ring 24 are slid into the furthest proximal position for insertion of needle 26. Needle 26 is inserted into barrel 22 and bonded therein by, for example, a crimped metal insert or epoxy.

Figure 11:
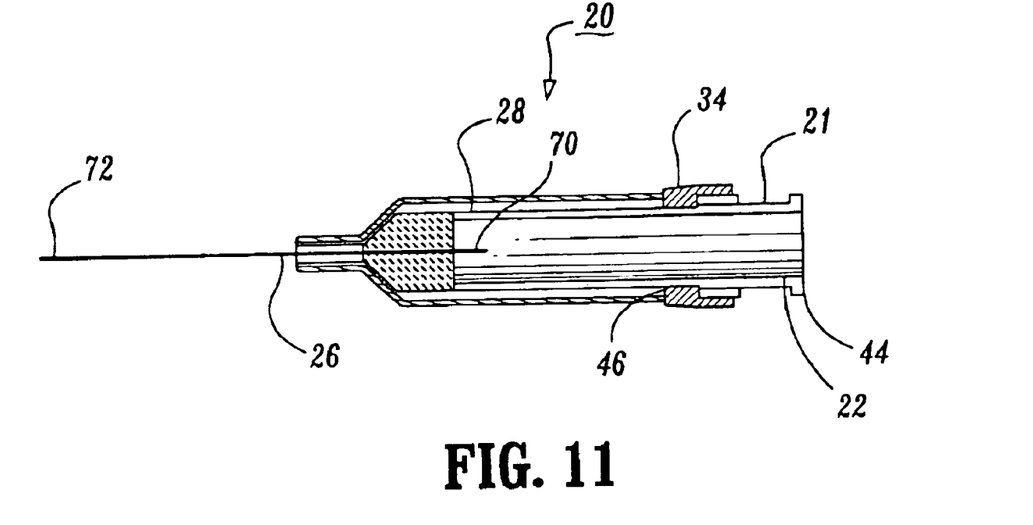
FIG. 11 is a side cross-sectional view of the safety needle apparatus shown in FIG. 1.
Figure 12:
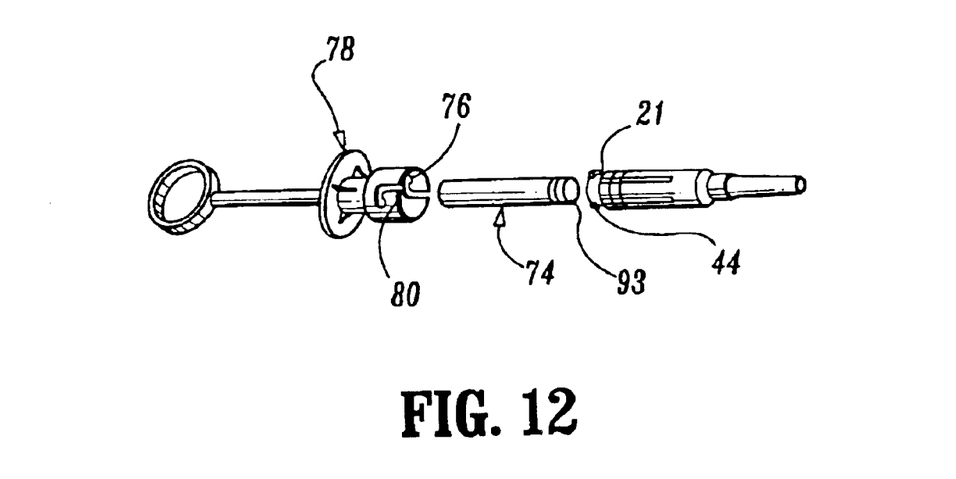
FIG. 12 is a perspective view of the safety needle apparatus shown in FIG. 1 mounted to a syringe adapter, with parts separated.

Referring to FIGS. 11 and 12, a proximal end 70 of needle 26 protrudes within barrel 22 for attachment to a drug containing cartridge, discussed below. Distal end 72 of needle 26 is exposed for injection. Needle sheath 30 (FIG. 1) is attached to cylindrical portion 91 of shield 28 and maintained by interference fit. A clinician is initially protected from proximal end 70 of needle 26 by barrel 22 and from distal end 72 by needle sheath 30.

A medication cartridge 74 is inserted with proximal end 21 of barrel 22. Medication cartridge 74 is forced in the distal direction until travel is prevented due to interference with distal end 23 of barrel 22. Proximal end 70 of needle 26 penetrates a diaphragm 93 of medication cartridge 74, which prepares cartridge 74 for use. Dental safety needle apparatus 20 is manipulated such that proximal tabs 44 of barrel 22 are slid into slots 76 of a syringe adaptor 78. Tabs 44 radially project from barrel 22 and are configured for receipt within cammed slots 76 of syringe adaptor 78 for mounting therewith. A retaining ring 80 secures dental safety needle apparatus 20 to syringe adaptor 78.

Figure 13:
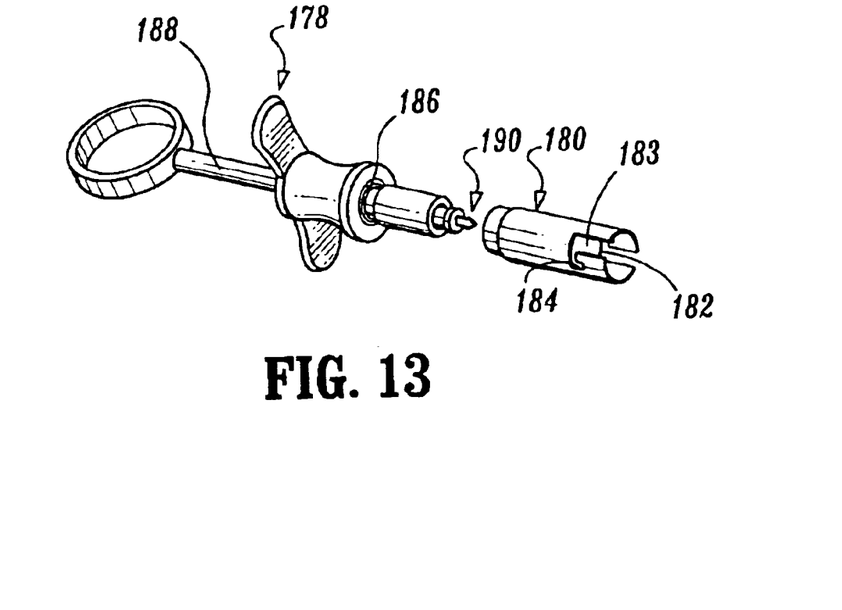
FIG. 13 is an enlarged perspective view of the syringe adapter shown n FIG. 12, with parts separated.
Figure 14:
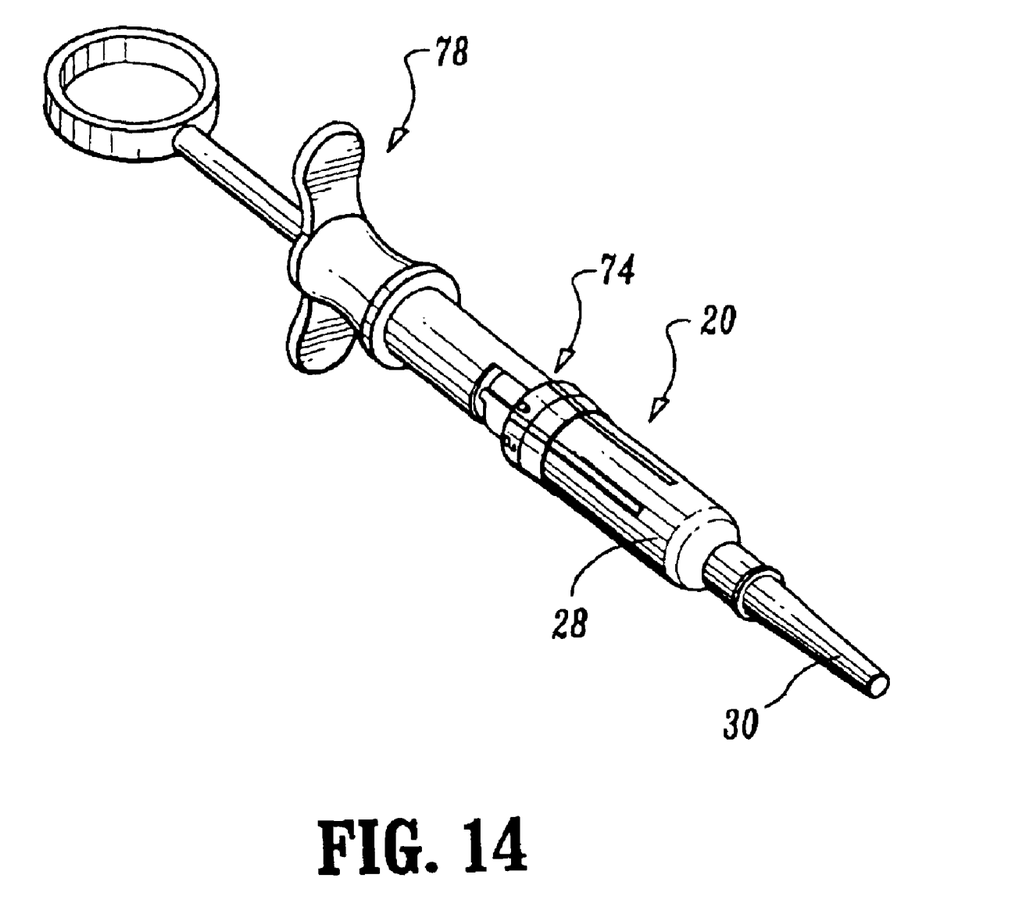
FIG. 14 is a perspective view of the safety needle apparatus shown in FIG. 1 mounted with the syringe adapter shown in FIG. 13.

Referring to FIG. 13, in an alternate embodiment, a syringe adaptor 178 is shown, which is configured for mounting with dental safety needle apparatus 20. Dental safety needle apparatus 20 and cartridge 74 (FIG. 12) are attached to an adaptor 180 by sliding tabs 44 of barrel 22 into slot 182 formed in a distal end of adaptor 180. Tabs 44 enter an open portion 183 of slot 182 and are rotated clockwise through a base portion 184 and released. A spring member 186, attached to a plunger 188, maintains dental safety needle apparatus 20 and cartridge 74 under compression.

Spring member 186 also maintains tabs 44 within slots 182. With tabs 44 within slots 182, shield 28 and lock ring 24 can be rotated clockwise or counter clockwise without disengaging dental safety needle apparatus 20 from adaptor 180. To remove dental safety needle apparatus 20 from adaptor 180, plunger 188 is pulled in a proximal direction to disengage a harpoon 190 from cartridge 74. Dental safety needle apparatus 20 is moved in the proximal direction and rotated counter clockwise until tabs 44 align with open portion 183. Dental safety needle apparatus 20 can be removed and discarded or a new cartridge 74 may be inserted for additional injections.

Figure 15:
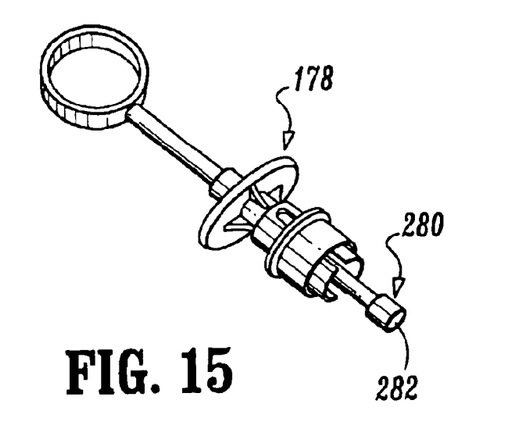
FIG. 15 is a perspective view of an alternate embodiment of a syringe adapter.
Figure 16:
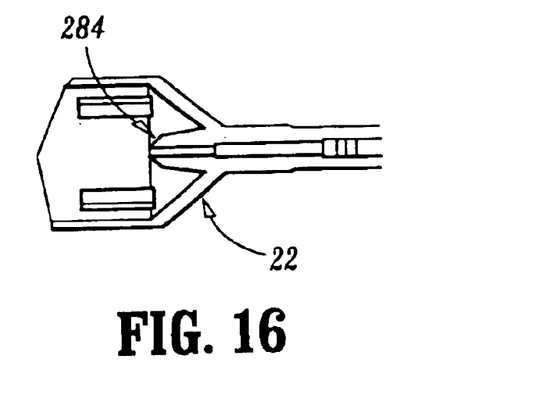
FIG. 16 is an alternate embodiment of a barrel for use with the syringe adapter shown in FIG. 15.

Referring to FIGS. 15 and 16, another alternate embodiment of syringe adaptor 178 is shown. Syringe adaptor 178 includes a plunger 280 having a blunt end 282. Blunt end 282 is configured for a self aspirating syringe whereby barrel 22 includes a projection 284. Projection 284 is configured to stretch a diaphragm of cartridge 74 upon injection to create back pressure for aspiration when plunger 280 is released. It is contemplated that this embodiment may be employed with harpoon, self aspirating, etc. syringe adaptors. It is contemplated that a flexible adaptor is attachable over a harpoon syringe adaptor to form a self aspirating device.

Figure 17:
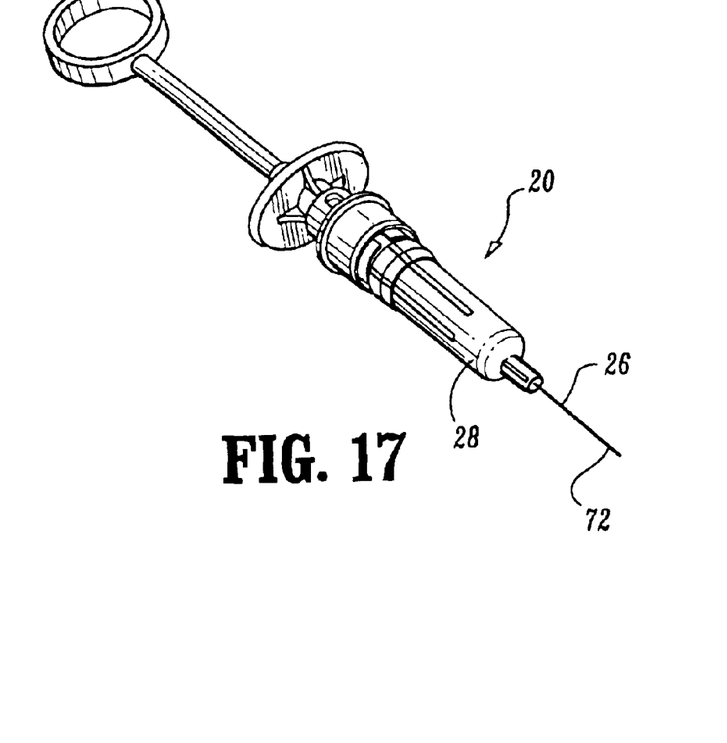
FIG. 17 is a perspective view of the safety needle apparatus mounted with the syringe adapter shown in FIG. 14, in an activated position.
Figure 18:
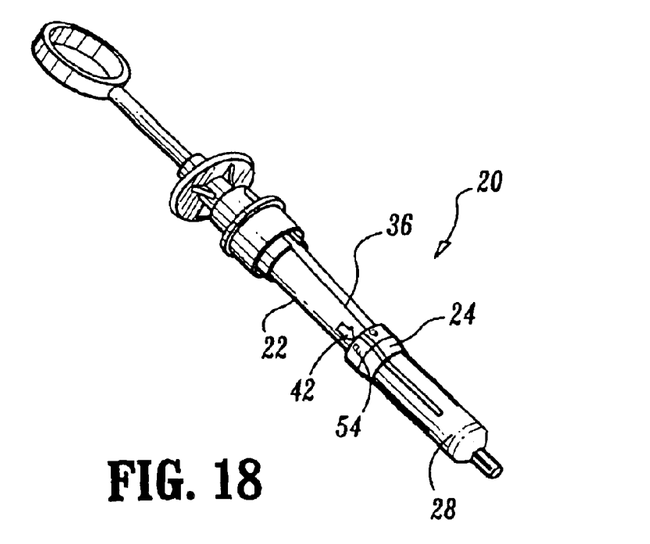
FIG. 18 is a perspective view of the safety needle apparatus mounted with the syringe adapter shown in FIG. 14, in a transport position.

Referring to FIGS. 14 and 17–19, dental safety needle apparatus 20, similar to that described above, is assembled as discussed, sterilized and otherwise prepared for storage, shipment and use. Dental safety needle apparatus 20 is attached to syringe adaptor 78 and medication cartridge 74, as discussed above. The clinician manipulates the needle sheath 30 in the distal direction. Needle sheath 30 engages shield 28 in an interference fit such that shield 28 slides forward with needle sheath 30 into the transport position (FIG. 18).

In the transport position, continued application of force on needle sheath 30 detaches needle sheath 30 from shield 28. Distal end 72 of needle 26 is protected by shield 28 to avoid hazardous exposure. Alternately, the clinician slides shield 28 into the transport position by manipulating shield 28 or lock ring 24 in the distal direction. In the transport position, needle sheath 30 is safely removed because shield 28 surrounds needle 26.

In use, a clinician (not shown) performs a medication (contained in medication cartridge 74) infusion to a subject (not shown) by manipulating shield 28 in a proximal direction such that long keys 46 (FIG. 11) of lock ring 24 overcome the interference of releasable stop 40 and slide inside keyways 36 of barrel 22. Long keys 46 slide to a frictional engagement with the proximal end of keyway 36 such that shield 28 and dental safety needle apparatus 20 are disposed in the activated position (FIG. 17). Distal end 72 of needle 26 is exposed for medication infusion to the subject.

Shield 28 may be returned to the transport position, for example, for administration of additional injections, transport, etc. by sliding shield 28 in the distal direction. The transport position is a releasably retained position and needle 26 is protected from hazardous exposure. In the transport position of dental safety needle apparatus 20, arrow 42 is aligned with unlocked symbol 54 of lock ring 24 indicating that shield 28 is releasably retained to enclose distal end 72 and not in the final lock position. Shield 28 can be moved back and forth between the transport position and the active position.

For example, in a dental procedure for administering anesthetic medication the clinician may set dental safety needle apparatus 20 aside and subsequently administer additional injections. Recapping needle 26 with needle sheath 30 is not required when dental safety needle apparatus 20 is the transport position. It is contemplated that arrow 42 may be molded with shield 28 and universal lock 52 or unlock 54 symbols can be molded with lock ring 24.

Figure 19:
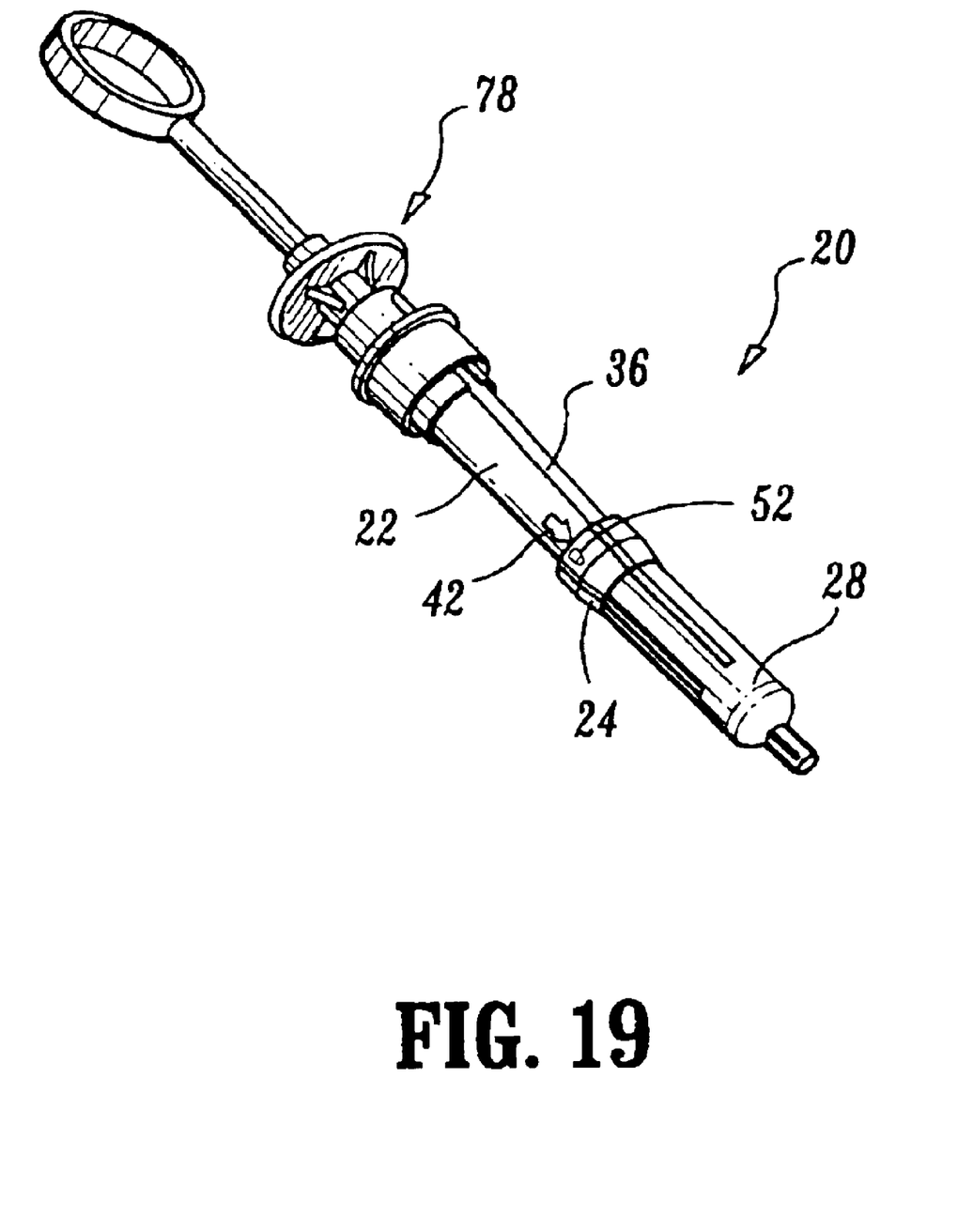
FIG. 19 is a perspective view of the safety needle apparatus mounted with the syringe adapter shown in FIG. 14, in a locked position.

Upon completion of all injections, dental safety needle apparatus 20 is manipulated to the final lock position, as shown in FIG. 19, for safe removal and disposal thereof. Shield 28 and/or lock ring 24 are manipulatively rotated approximately 45° in the clockwise or counter-clockwise direction, as discussed, until long keys 46 become fixedly disposed in locking slots 36. Tactilely, the clinician feels a snap as keys 46 enter slots 36. Visually, arrow 42 on shield 28 is aligned with lock symbol 52. An audible sensation is heard upon snapping of long keys 46.

In the final lock position, shield 28 can not be retracted to expose distal end 72 of needle 26 and dental safety needle apparatus 20 is safe for removal from syringe adaptor 78 and disposal. Other methods of employing dental safety needle apparatus 20 are also envisioned.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A safety needle apparatus including a needle, the safety needle apparatus comprising:

a first cylinder extending from a proximal end to a distal end thereof and defining a longitudinal axis, the first cylinder further defining at least one longitudinal keyway in a side wall thereof and a plurality of keyslots disposed adjacent the distal end of the first cylinder and rotationally spaced apart from the at least one keyway relative to the longitudinal axis, wherein the at least one keyway includes a raised surface relative to and disposed adjacent the distal end of the first cylinder; and a shield mounted for relative movement with the first cylinder and defining a plurality of radially projecting keys adjacent a proximal end thereof, at least one of the keys being configured for axial movement along the keyway such that the shield is movable between an activated position, whereby the at least one of the keys is releasably engaged with a proximal end of the at least one keyway to expose the needle, and a transport position, whereby the at least one of the keys is releasably disposed adjacent the distal end of the first cylinder via an interference engagement with the raised surface of the first cylinder to releasably enclose the needle within the shield, the shield being further movable from the transport position to a locked position, whereby the at least one of the keys is rotated relative to the first cylinder for fixed disposal within the at least one keyslot to fixedly enclose the needle within the shield.

2. A safety needle apparatus as recited in claim 1, wherein the first cylinder is a barrel and the shield is mounted to an outer surface of the barrel.

3. A safety needle apparatus as recited in claim 1, wherein the shield is elongated and configured to enclose the needle, the shield having a lock ring mounted to a proximal end thereof, the lock ring defining the plurality of keys about an inner circumferential surface thereof.

4. A safety needle apparatus as recited in claim 3, wherein the shield includes at least one proximally extending tab that facilitates mounting of the shield within the lock ring.

5. A safety needle apparatus as recited in claim 4, wherein the at least one tab is flexibly cantilevered from the shield.

6. A safety needle apparatus as recited in claim 3, wherein the shield includes a plurality of proximally extending tabs that facilitate mounting of the shield within the lock ring.

7. A safety needle apparatus as recited in claim 3, wherein the lock ring mounts with the shield via disposal of the plurality of keys within a plurality of axial slots defined by the proximal end of the shield.

8. A safety needle apparatus as recited in claim 7, wherein the plurality of keys are equidistantly spaced for corresponding disposal within the plurality of axial slots of the shield.

9. A safety needle apparatus as recited in claim 8, wherein the proximal end of the shield includes a radial lip that engages the lock ring to facilitate retention therewith.

10. A safety needle apparatus as recited in claim 1, wherein the shield is movable from the transport position to the locked position such that the plurality of keys are rotatable in a clockwise direction and a counter clockwise direction relative to the first cylinder for fixed disposal within the plurality of keyslots to fixedly enclose the needle within the shield.

11. A safety needle apparatus as recited in claim 1, wherein the first cylinder defines a reduced diameter cylindrical portion extending from the distal end thereof, a distal end of the shield being configured and dimensioned to receive an outer surface of the cylindrical portion of the first cylinder in a contacting engagement.

12. A safety needle apparatus as recited in claim 11, wherein the cylindrical portion of the first cylinder has a circumferential lip that engages the distal end of the shield in an interference fit configured to form a moisture barrier.

13. A safety needle apparatus as recited in claim 1, wherein the first cylinder and the shield include visual indicia that cooperate to provide a visual indication that the shield is in the locked position.

14. A safety needle apparatus as recited in claim 1, wherein the proximal end of the first cylinder includes at least one radially projecting tab, the tab of the first cylinder being configured for receipt within a cammed slot of a syringe plunger adapter for mounting therewith.

15. A dental safety needle apparatus including a needle, the safety needle apparatus comprising:

a barrel extending from a proximal end to a distal end thereof and defining a longitudinal axis, the barrel further defining at least one longitudinal keyway in a side wall thereof and at least one keyslot disposed adjacent the distal end of the barrel and rotationally spaced apart from the at least one keyway relative to the longitudinal axis, wherein the at least one keyway includes a raised surface relative to and disposed adjacent the distal end of the barrel; and a shield mounted for relative movement with the barrel and including a locking means for engagement with the at least one keyway to facilitate movement of the shield between an activated position, whereby the needle is exposed, and a transport position, whereby the shield releasably encloses the needle, the locking means engaging the at least one keyslot to facilitate movement of the shield from the transport position to a locked position, whereby the shield fixedly encloses the needle.

16. A dental safety needle apparatus as recited in claim 15, wherein the barrel defines a reduced diameter cylindrical portion extending from the distal end thereof, a distal end of the shield being configured and dimensioned to receive an outer surface of the cylindrical portion of the barrel in a contacting engagement.

17. A dental safety needle apparatus as recited in claim 16, wherein the cylindrical portion of the barrel has a circumferential lip that engages the distal end of the shield in an interference fit configured to form a moisture barrier.

18. A dental safety needle apparatus as recited in claim 15, wherein the barrel and the shield include visual indicia that cooperate to provide a visual indication that the shield is in the locked position.

19. A dental safety needle apparatus including a double-ended needle cannula, the dental safety needle apparatus comprising:

a barrel extending from a proximal end to a distal end thereof and defining a longitudinal axis, the barrel further defining a pair of diametrically disposed longitudinal keyways in a sidewall thereof and a plurality of keyslots disposed adjacent the distal end of the barrel, the keyslots being rotationally spaced apart from the keyways relative to longitudinal axis, the keyways including a raised surface relative to and disposed adjacent to the distal end of the barrel, the barrel having a reduced diameter barrel tip extending from the distal end thereof;

a shield mounted for relative movement with the barrel and including a lock ring mounted to a proximal end thereof, the lock ring having a pair of diametrically disposed radially projecting keys, the keys being configured for axial slidable movement along the keyways of the barrel such that the shield is movable between an activated position, whereby the keys are releasably engaged with proximal ends of the keyways to expose the double-ended needle cannula, and a transport position, whereby the keys are releasably disposed adjacent the distal end of the barrel via an interference engagement with the raised surface of the barrel to releasably enclose the double-ended needle cannula within the shield, the shield being further movable from the transport position to a locked position such that the keys are rotatable in a clockwise direction and a counter clockwise direction relative to the barrel for fixed disposal within the plurality of keyslots to fixedly enclose the double-ended needle cannula within the shield, the lock ring including raised longitudinal ribs circumferentially disposed thereabout.

20. A safety needle apparatus including a needle, the safety needle apparatus comprising:

a first cylinder extending from a proximal end to a distal end thereof and defining a longitudinal axis, the first cylinder further defining at least one longitudinal keyway in a side wall thereof and at least one keyslot disposed adjacent the distal end of the first cylinder and rotationally spaced apart from the at least one keyway relative to the longitudinal axis, wherein the at least one keyway includes a raised surface relative to and disposed adjacent the distal end of the first cylinder; and a second cylinder mounted for relative movement with the first cylinder and defining at least one radially projecting key adjacent a proximal end thereof, the at least one key being configured for axial movement along the keyway such that the second cylinder is movable between an activated position, whereby the at least one key is releasably engaged with a proximal end of the at least one keyway to expose the needle, and a transport position, whereby the at least one key is releasably disposed adjacent the distal end of the first cylinder via an interference engagement with the raised surface of the first cylinder to releasably enclose the needle within the second cylinder, the second cylinder being further movable from the transport position to a locked position, whereby the at least one key is rotated relative to the first cylinder for fixed disposal within the at least one keyslot to fixedly enclose the needle within the second cylinder, wherein the first cylinder defines a reduced diameter cylindrical portion extending from the distal end thereof, a distal end of the second cylinder being configured and dimensioned to receive an outer surface of the cylindrical portion of the first cylinder in a contacting engagement.

* * * * *